United States Patent
Wojcik et al.

[19]

[11] Patent Number: 5,860,968
[45] Date of Patent: Jan. 19, 1999

[54] LASER SCANNING METHOD AND APPARATUS

[75] Inventors: Steven E. Wojcik, Lynnwood; Edward S. Schieferstein, Everett; Michael B. Levy, Woodinville, all of Wash.

[73] Assignee: Luxar Corporation, Bothell, Wash.

[21] Appl. No.: 552,555

[22] Filed: Nov. 3, 1995

[51] Int. Cl.⁶ .................................................. A61B 17/36
[52] U.S. Cl. ............................... 606/10; 606/16; 606/17; 607/93
[58] Field of Search .................................. 606/2, 3, 9, 10, 606/13, 16–19; 607/88, 89, 93; 359/196–198, 200, 209; 250/227.26, 236

[56] References Cited

U.S. PATENT DOCUMENTS

| | | | |
|---|---|---|---|
| 4,266,548 | 5/1981 | Davi | 606/17 |
| 4,733,660 | 3/1988 | Itzkan | 606/9 |
| 5,133,035 | 7/1992 | Hicks | 385/117 |
| 5,336,217 | 8/1994 | Buys et al. | 606/9 |
| 5,400,428 | 3/1995 | Grace | 606/16 |
| 5,409,483 | 4/1995 | Campbell et al. | 606/15 |
| 5,411,502 | 5/1995 | Zair | 606/10 |
| 5,628,744 | 5/1997 | Coleman et al. | 606/12 |
| 5,733,277 | 3/1998 | Pallarito | 606/16 |

*Primary Examiner*—John P. Lacyk
*Assistant Examiner*—Bryan K. Yarnell
*Attorney, Agent, or Firm*—Seed And Berry LLP

[57] ABSTRACT

A laser scanning method and apparatus having a scanning hand piece 18 connected at the free end 20 of a hollow wave guide 14 to scan a beam of laser energy 22 in a predetermined pattern to uniformly ablate in an enlarged target area. The hand piece 18 includes a hollow shaft motor 40 having a conduit mounted therein for conducting the beam of laser energy 22. The conduit 54 has a proximal end 56 in axial alignment with the longitudinal axis 60 of the hollow shaft 48 and in light energy communication with the laser energy generator 12. The distal end 58 of the conduit 54 is mounted in the hollow shaft 48 so that it is eccentrically positioned with respect to the axis 60 of the hollow shaft 48. When the motor 40 is energized, the hollow shaft 48 rotates the distal end 58 of the conduit 54 in a predetermined circular pattern to scan the laser energy uniformly and thoroughly over the tissue in the target area.

16 Claims, 4 Drawing Sheets

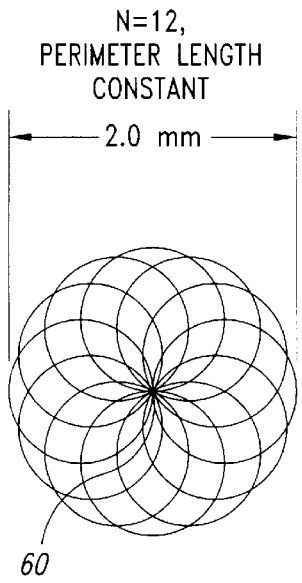
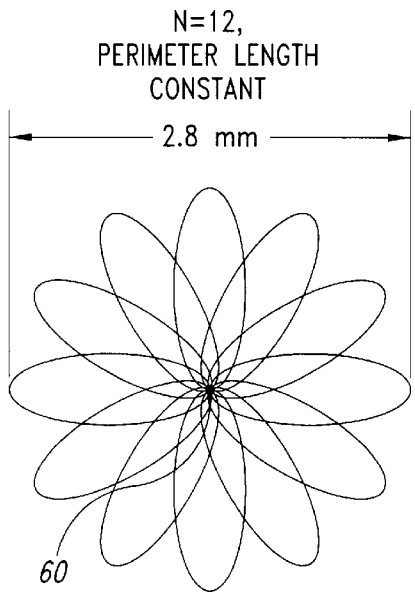
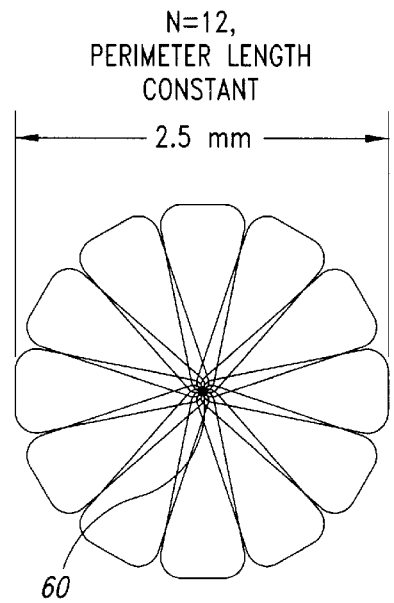
*Fig. 5A*        *Fig. 5B*        *Fig. 5C*
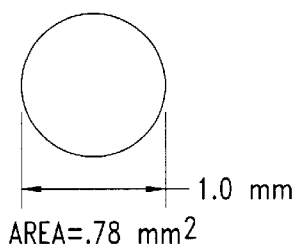
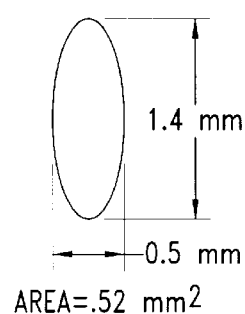
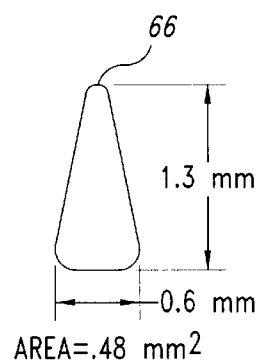
*Fig. 6A*        *Fig. 6B*        *Fig. 6C*

LASER SCANNING METHOD AND APPARATUS

TECHNICAL FIELD

The present invention pertains to the uniform delivery of laser energy to a target site, and, more particularly, to a method and apparatus for moving a beam of laser energy in a predetermined pattern to thoroughly cover a target site and achieve uniform ablation of tissue.

BACKGROUND OF THE INVENTION

The carbon dioxide ($CO_2$) laser beam has been used for many years in the ablation of living tissue. The $CO_2$ laser causes a temperature rise in the tissue primarily due to the absorption of laser radiation by water in the tissue. When this water is heated to its boiling point, it causes an explosive ablation of the surrounding tissue. However, heat transfer to adjacent tissue may cause thermal damage, resulting in tissue necrosis, desiccation, or carbonization ("char") that hinders further ablation until the "charred" tissue is removed. One technique to minimize damaging heat transfer to adjacent, unablated tissue is to cause a rapid temperate rise in irradiated tissue.

One technique that has been developed to cause a rapid temperature rise in irradiated tissue and to minimize thermal damage in adjacent tissue is generically referred to as "superpulse" operation of the $CO_2$ laser. Superpulse operation involves rapidly heating the irradiated tissue with pulsed laser energy followed by a period of no exposure to laser energy, which gives time for the heat in the non-ablated adjacent tissue to dissipate. The irradiance of the laser beam must be high enough for the absorbed energy to rapidly vaporize water in the target tissue and create an explosive ablation.

In theory, in order to create explosive ablation, tissue irradiance must be above 40 watts/mm$^2$. However, in practice an irradiance of 70 watts/mm$^2$ or greater is generally used.

For tissue with a thermal relaxation time of approximately 325 microseconds, the pulse duration of the laser in the superpulse monde is limited to a range of about 150 to 900 microseconds. The "off" time between pulses is typically a minimum of ten time constants or greater than 3.3 milliseconds. While increasing the off time between pulses allows more time for tissue to cool, it has the disadvantage of lowering average power and tissue ablation rates.

The maximum spot size of "char-free" superpulsed ablation is generally limited by the peak power of the laser system being used. The peak power required for superpulse ablation increases by the square of the diameter of the spot. For example, in order to ablate a two-millimeter diameter area, the laser system must be capable of delivering 20 watts of peak power, while a 3 mm spot would require 500 watts peak power. Therefore, to ablate large areas with a laser system having limited peak power, it is necessary to scan the beam over the large area, either by hand or using some type of scanning device. Presently, medical $CO_2$ laser systems traditionally rely on articulated arms that have the disadvantage of being bulky and using awkward multi-segmented tubes with rotating mirrored joints to deliver the laser energy from the laser console to the treatment site.

Flexible hollow wave guides have been developed that have a more "fiber-like" feel to replace these articulated arms. The disadvantage to such hollow wave guides is they tend to have an energy distribution that is typically non-gaussian or multi-mode and changes as the wave guide is bent. Within a few millimeters of the distal end of the wave guide, the effect of the multi-mode output energy is insignificant. This is because tissue tends to integrate laser energy over small areas and produce fairly uniform "char-free" ablation if the laser is operated in a superpulse mode. However, as the distance between the end of the wave guide and the tissue increases, the output beam diverges to create a large spot size. The increased spot size not only requires increased peak power, but the multi-mode nature of the wave guide output can produce non-uniform ablation. Therefore, it is desirable to maintain a short distance between the end of the wave guide and the target tissue to achieve uniform ablation. This has the disadvantage of limiting the maximum usable spot size even though there is sufficient peak power to ablate larger areas with a single pulse of laser energy.

One solution is to maintain a small spot size and close distance to the target tissue and rapidly move the small beam of laser energy over the target area. A great deal of manual dexterity and experience is required to accomplish uniform ablation over a large area by hand. One proposed mechanical method for doing so is disclosed in U.S. Pat. No. 5,411,502 issued to Zair on May 2, 1995, which is directed to a system using one or two electromechanically rotated mirrors in combination with a focusing lens to cause the laser beam to trace Lissajous figures. The drawbacks to this system are the cumbersome and complex mechanical components and the effort required to maintain the mirrors and focusing lens in precise alignment. In addition, this proposed system does not address compatibility with pulsed laser beam radiation or flexible hollow wave guide systems.

Consequently, there is a need for a mechanically simple system for uniformly and thoroughly scanning a large target area with a beam of laser energy.

SUMMARY OF THE INVENTION

The present invention is directed to a laser scanning method and apparatus to uniformly deliver the beam of laser energy to a target site. In accordance with the present invention, the method for uniformly scanning a laser beam involves uniformly moving the beam of laser energy in a predetermined pattern over the target site. In one form of the invention, the beam is moved by manipulating conduit through which the beam travels, with the proximal end of the conduit being held in fixed alignment with the laser energy source and the distal end of the conduit being moved in a predetermined pattern.

In accordance with another aspect of the present invention, the method further involves the step of holding the conduit in a predetermined shape and rotating the conduit such that the proximal end remains in fixed alignment with the rotational axis and the distal end rotates eccentrically with respect to the rotational axis. More preferably, the distal end rotates in a circular pattern around the rotational axis.

In accordance with yet another aspect of the of the present invention, the laser energy source is pulsed at a predetermined power level and for a predetermined frequency and duration, and the conduit is moved at a predetermined speed in coordination with the pulses of laser energy to uniformly scan the laser beam over the target area and achieve uniform tissue ablation in the target area.

The present invention is further directed to a laser delivery system that comprises a generator of laser energy, a guide for conducting the laser energy to a target site; and a device for scanning the laser energy at the target site, the scanning device comprising a conduit for conducting laser energy; and a device for moving the conduit in a predetermined pattern to uniformly scan the target site with laser energy and achieve a uniform and thorough ablation of the target tissue at the target site.

In accordance with another aspect of the present invention, the conduit has a proximal end in light energy communication with the guide and a distal end mounted on the moving device. Ideally, the distal end has a predetermined cross-sectional configuration that is substantially triangular or teardropped shaped.

In accordance with yet another aspect of the present invention, the conduit is elongated and has a longitudinal axis, and the conduit is mounted on the moving device such that the proximal end of the conduit rotates about its longitudinal axis and the distal end is off center in relation to the longitudinal axis of the proximal end whereby the moving device moves the distal end in a circular pattern around the longitudinal axis. Ideally, the moving device comprises a motor having a hollow rotator shaft with the conduit mounted in the shaft.

In accordance with yet another aspect of the present invention, the laser generator is configured to generate pulses of laser energy of a predetermined power, frequency and period or duration, and the moving device is configured to move the distal end of the conduit at a predetermined continuous speed in coordination with the frequency and duration of the laser energy pulses so that the laser energy is delivered uniformly to the target site.

In accordance with still yet another aspect of the present invention, a laser scanning device for delivering laser energy from a laser energy source to a large target site is disclosed. The device includes a laser energy conduit for conducting laser energy to the target site; and an apparatus for moving the conduit in a predetermined pattern to uniformly and thoroughly scan the target area with laser energy to achieve a uniform ablation of tissue at the target site. Ideally, the conduit has a proximal end in laser energy communication with the laser energy source and a distal end having a predetermined cross-sectional configuration that is either substantially triangular or teardropped shaped.

In accordance with yet another aspect of the present invention, the moving apparatus includes a hollow shaft that rotates about its longitudinal axis and further wherein the conduit is mounted within the hollow shaft such that the distal end rotates eccentrically with respect to the longitudinal axis of the hollow shaft, and, more preferably, rotates around the longitudinal axis of the hollow shaft in a circle.

In accordance with a further aspect of the present invention, the laser energy source is configured to deliver pulses of laser energy of predetermined power, frequency and period or duration, and the moving apparatus is further configured to move the conduit at a speed that is coordinated with the pulses of laser energy to achieve a uniform scanning of laser energy at the target site to thereby uniformly ablate tissue at the target site.

As will be readily appreciated from the foregoing, the present invention provides a simplified mechanical apparatus for moving a beam of laser energy in a predetermined pattern without requiring any flexing of the conduit, thus avoiding fatigue failure of the conduit. In addition, the method and apparatus of the present invention utilizes compact, lightweight components requiring minimal outside energy and little skill on the part of the operator. This results in a more uniform delivery of the laser beam energy to the tissue at the target site.

BRIEF DESCRIPTION OF THE DRAWINGS

The foregoing and other features and advantages of the present invention will be more readily appreciated as the same becomes better understood from the following detailed description, wherein:

FIGS. 5A–C are illustrations of target areas covered by circular, oblong, and triangular or teardropped shaped configurations of the distal end of the conduit, respectively; and FIGS. 6A–C are representations of circular, oblong, and triangular or teardropped shaped cross-sectional configurations for the distal end of the conduit.

DETAILED DESCRIPTION

Figure 1:
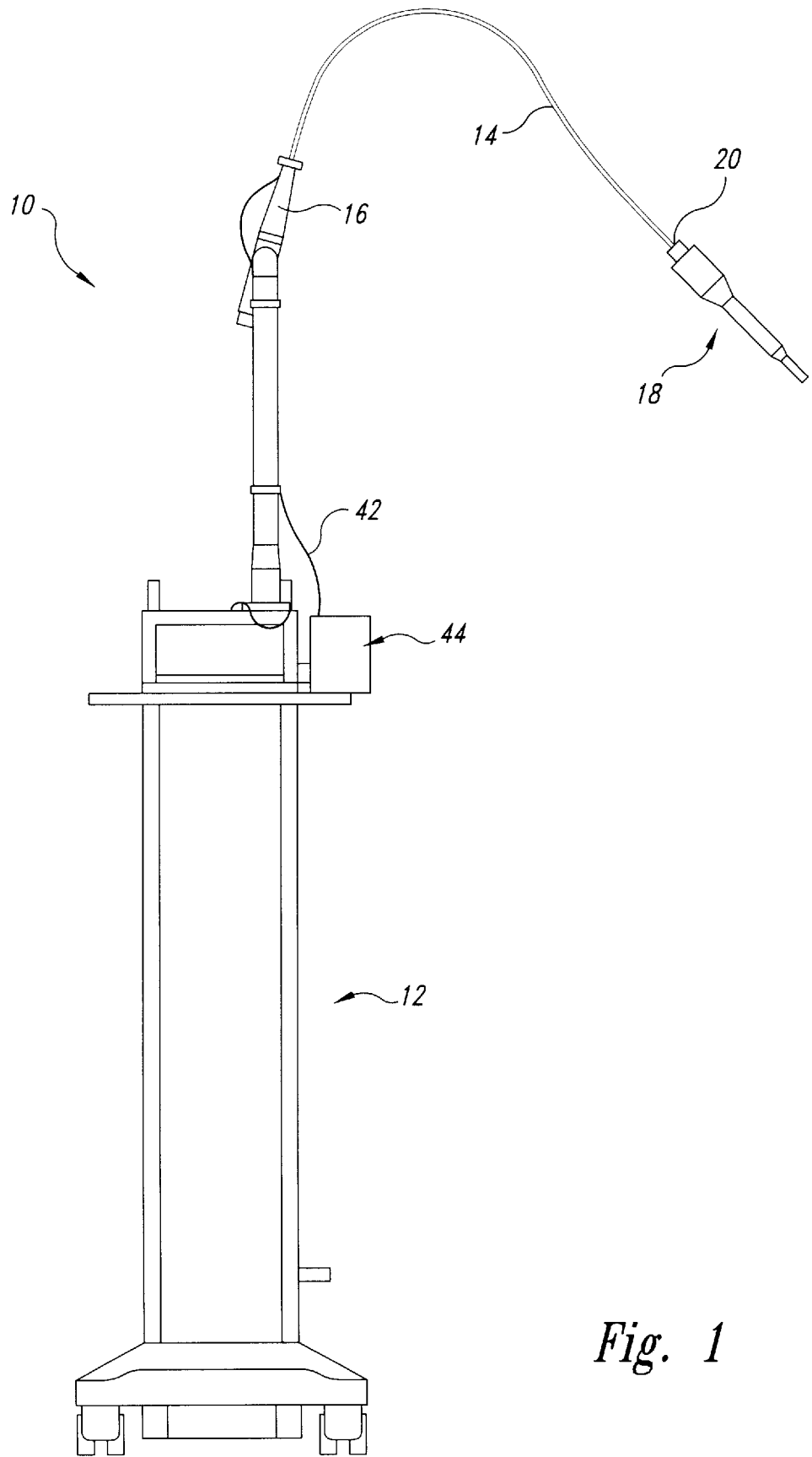
FIG. 1 is plan view of a laser delivery system formed in accordance with the present invention.

Referring initially to FIG. 1. shown therein is a laser delivery system 10 generally comprising a laser energy generator 12 for generating a beam of laser energy, which is conducted through a flexible hollow wave guide 14 that is supported on the generator 12 by a support arm 16. A scanning hand piece 18 is connected at the free end 20 of the hollow wave guide 14. The beam of laser energy 22 exits the hand piece 18 (shown out of proportion in FIG. 2 for illustration purposes only). The generator 12 is ideally configured to generate pulses of laser energy as described more fully below. However, the present invention may also be used with continuous beam laser generators.

Figure 2:
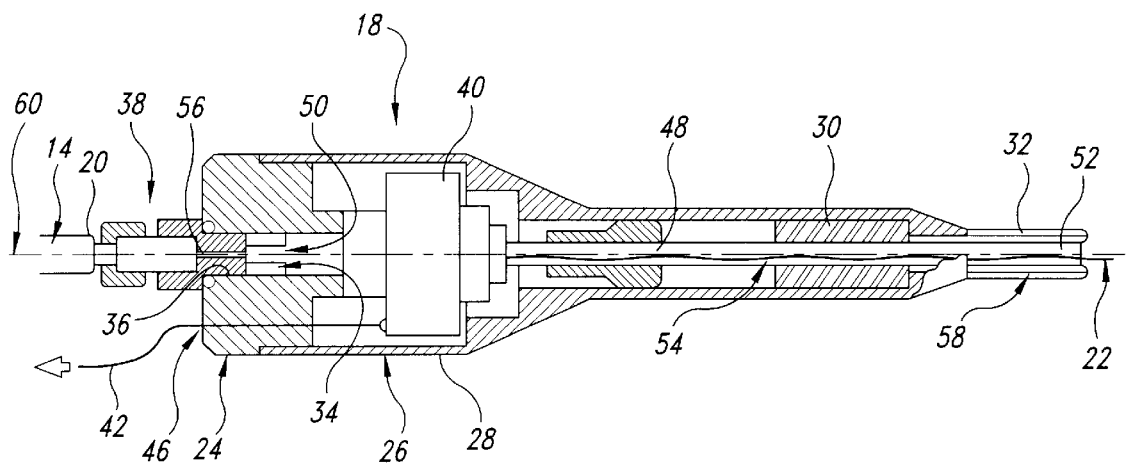
FIG. 2 is a cross-sectional view of a laser scanning device formed in accordance with the present invention.

Referring, next to FIG. 2, illustrated therein is an enlarged cross-sectional view of the hand piece 18, which comprises a base 24 threadably connected to a cylindrical housing 26. The housing has an enlarged motor section 28 that reduces down to an extended main section 30 that in turn reduces down to an elongated nose section 32. The base 24 has a centrally disposed cylindrical bore 34. The bore 34 has internal threads 36 that are adapted to receive an externally threaded coupling unit 38. The free end 20 of the hollow wave guide 14 is attached to the housing base 24 via the coupling unit 38 such that the laser beam energy is in communication with the bore 34 in the base 24.

A motor 40 is mounted on the base 24 and has a control cable 42 that extends through an access opening 46 in the base 24. The control cable 42 is connected to a control 44 unit on the generator 12. It is to be understood that the motor control unit 44 may be integral to the hand piece 18 or mounted remotely (as shown) to minimize the weight of the hand piece 18.

The motor 40 is a hollow shaft DC electric or stepper motor that is selected for its compactness and simplicity and is readily commercially available. However, any type of motor can be used, such as an air or hydraulic motor or an electric motor rotating the hollow shaft 48 through a gear, belt, or friction drive arrangement. The hollow shaft 48 is centrally disposed within the motor 40. A proximal end 50 of the shaft 48 projects into the bore 34 of the base so that it is in light energy communication with the generator 12 through the wave guide 14. The hollow shaft 48 is rotatably mounted in the extended main section 30 of the housing and has a distal end 52 that projects into the nose section 32.

Mounted within the hollow shaft 48 is a conduit 54 for conducting the beam of laser energy 22. The conduit 54 has a proximal end 56 that extends out the proximal end 50 of the hollow shaft 48 and into the central bore 34 of the housing base 24. The conduit 54 is preferably a hollow light pipe having the central axis at its proximal end 56 in alignment with the central axis 60 of the hollow shaft 48. Such light pipes are readily commercially available. However, the distal end 58 is positioned in the hollow shaft 48 so that it is eccentrically mounted (not aligned) with respect to the axis 60 of the hollow shaft 48. This is shown more clearly in FIG. 3.

Figure 3A:
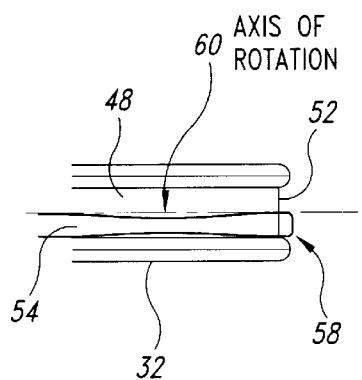
FIGS. 3A and 3B are an enlarged partial cross-sectional side view and end view, respectively, of the conduit mounted in the hollow shaft.
Figure 3B:
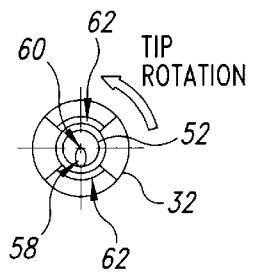

In order to facilitate alignment of the light beam 22 with a target site, an aiming and distance guide in the form of an opening 62 is created in the nose section 32 of the housing 26. Preferably, the guide 62 is formed on opposing sides of the nose section 32, as shown in FIG. 3. This enables line of sight aiming and distance judging by the user when placing the hand piece at or on the target site and therefore facilitates optimum spacing from the target site. Ideally, the distance between the distal end 58 of the conduit 54 and the target area will be in the range of 0 to 3 mm.

As shown in FIG. 3, as the motor 40 rotates the shaft 48 and conduit 54 in the direction of rotation shown by the arrow 64, the distal end 58 of the conduit 54 traces a circular pattern. If the distal end 58 of the conduit 54 is positioned eccentrically so that its axis is about one conduit radius from the axis 60, the scanned pattern will be twice the diameter of the conduit's distal end 58.

The cross-sectional configuration of the distal end 58 of the conduit is preferably teardropped shaped, as shown in FIG. 6C. This shape is substantially in the form of an isosceles triangle, and when used with the present invention, the apex 66 will be mounted at least adjacent to the axis 60 of rotation. When so mounted and rotated by the motor 40, the conduit 54 will scan the beam 22 of laser energy in a circular pattern to cover a target area depicted in FIG. 5C.

Similarly, the oval shape depicted in FIG. 6B will cover a target area shown in FIG. 5B, and the circular shape shown in FIG. 6A will cover an area depicted in FIG. 5A.

In operation, the motor 40 rotates the hollow shaft 48 with the conduit 54 mounted therein. When the conduit 54 rotates, the longitudinal axis of the conduit 54 at the proximal end 56 will be in alignment with the axis 60 of the hollow shaft 48. However, the distal end 58 of the conduit 54 will be eccentric with respect to the axis 60 and rotate in a circle around the axis 60, as described above.

The distal end 58 of the conduit 54 will rotate at a constant angular rotation ω, Hertz ("Hz"), with an associated period of rotation T (in seconds). The beam 22 of laser energy from the $CO_2$ generator 12 is ideally emitted in pulses having a frequency f (in Hertz), with a duration or pulse width of t (in seconds), at a peak power of P (in watts). It is to be understood, however, that the present invention may be used with a constant emission of laser energy, as will be readily ascertainable by one of ordinary skill in the art.

The frequency is chosen such that the number of pulses per revolution, N, provides uniform coverage of the scanned diameter D (in mm). The required repetition frequency of laser pulses is:

$$f = (1/T) = \omega \times N$$

Figure 4:
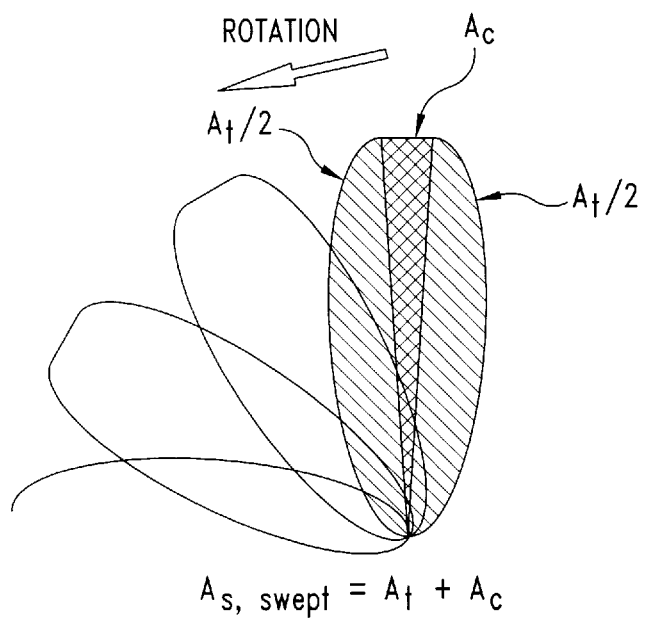
FIG. 4 is an illustration of area covered using one configuration of the distal end of the conduit.

To provide "char-free" ablation, the irradiance I should exceed 40 watts/mm² and t (the pulse duration), should be less than 900 microseconds. Since the distal end 58 of the conduit 54 is constantly moving relative to the target tissue, the area scanned with the laser energy during each pulse is the swept area $A_s$ mm², rather than the area of the tip $A^t$ mm². This is shown in FIG. 4, and can be calculated as follows:

$$A_s = A_t + A_c \text{ where } A_c = (t \times \omega \times \pi \times D^2)/4$$

so that the irradiance is $I = P/A_s$ watts/mm² and the average power is $P_{ave} = (P \times t)/T$ The energy per unit area, referred to as the fluence F, must also exceed 40 mJ/mm². This parameter effectively sets the minimum pulse width for t such that:

ti $F = (P \times t)/A_2$ and then $t_{min} = (F \times A_s)/P$

The tissue depth removed per pulse z (in mm), can be estimated by:

$$z = (F_{th})/J_{th}$$

where fluence threshold is $F_{th}$=40 mJ/mm² and the energy threshold per unit volume is $J_{th}$=3000 mJ/mm³.

The depth of tissue removed can then be easily controlled by gating the laser energy output to occur for an integral number of revolutions of the motor such that:

$$Z_{total} = n_{rev} \times z$$

and the "on" time of the gated laser output burst is:

$$T_{gated} = n_{rev}/\omega$$

where $n_{rev}$ is an integral number.

It should be noted that a major advantage of the method of the present invention is that the laser energy output from the generator 12 need not be synchronized to the position of the rotating tip. Gating the laser's output time equal to the period of an integral number of motor revolutions simplifies the control scheme and allows the scanning hand piece 18 to be added to an existing laser system without modification.

The distal end 58 of the conduit 54 need not have a circular cross-section, as described above. In fact, there are advantages to using conduits 54 in which the circular cross-section of the distal end 58 is distorted to an elliptical or teardrop shape. Forming the tip to an elongated shape decreases the cross-sectional area relative to a circular tip of equal circumference, thus increasing the irradiance. This in turn reduces the system power required to meet the threshold of superpulse irradiance. Elongating the tip also increases the swept area if the ellipse or teardrop is positioned such that the point of smallest curvature (the apex 66 shown in FIG. 6C) is on or substantially adjacent the axis of rotation 60. An elongated distal end 58 also fills the swept area with less overlap between pulses for more uniform target tissue ablation.

By modifying the distal end 58 to have different amounts of eccentricity and/or shape, a variety of scanned spot sizes may be easily obtained. Since these conduits 58 are readily available and have a relatively low cost to fabricate, they can be sterilized for single use to simplify infection control.

EXAMPLE

The system 10 described above was built and tested based on a Luxar LX-20 SP Novapulse $CO_2$ laser system. The laser energy generator 12 uses a hollow flexible wave guide delivery system 14 and can be operated in superpulse modes capable of delivering gated 50 watt peak pulse trains having pulse widths between 500 and 900 microseconds. The nominal inside diameter of the flexible hollow wave guide 14 and conduit 54 is 1.0 millimeter providing an effective spot diameter of 0.8 millimeters.

The distal end 58 of the rotating conduit 54 is deformed from a cross-section of 0.79 mm² to a triangular or teardrop shape of 0.48 mm². The number of pulses per revolution N was chosen empirically to provide relatively uniform coverage of the 2.5 mm diameter scanned target area with minimal overleap between pulses. Laser pulses are repeated every five milliseconds, allowing a minimum cooling time between pulses of:

$$T_{cooling} = T - t = 5 \text{ ms} - 900 \text{ microseconds} = 4.1 \text{ ms},$$

or 4.1 ms/325 microseconds=13 thermal relaxation time constants.

The laser pulse frequency is:

$$f = 1/5 \text{ ms} = 200 \text{ Hz}$$

The motor speed is:

$$\omega = 1/(N \times T) = 1/12 \times 5 \text{ ms}) = 16.7 \text{ Hz} = 1000 \text{ RPM}$$

The swept area for t=500 to 900 microseconds is:

$$A_s = 0.48 \text{ mm}^2 + [(0.9 \text{ ms}/(12 \times 5 \text{ ms})) \times (\pi \times (2.5 \text{ mm}^2)/4)] = 0.53 \text{ to } 0.56 \text{ mm}^2$$

The average power can be adjusted by varying t. For t=500 to 900 microseconds, average power will be:

$$P_{ave} = 50 \text{ watts} \times t/5 \text{ ms} = 5 \text{ to } 9 \text{ watts}$$

The fluence (for t=500–900 microseconds) is:

$$F = (50 \text{ watts} \times t)/0.56 \text{ mm}^2 = 48 \text{ to } 80 \text{ mJ/mm}^2$$

The depth of tissue removed per revolution is:

$$z = (F - 40 \text{ mJ/mm}^2)/3000 \text{ mJ/mm}^3 = 3 \text{ to } 13 \text{ micrometers per revolution}$$

By gating the laser signal in integral numbers of revolution times $1/\omega$ (i.e., 60, 120, 180, 240 milliseconds), tissue can be removed to any desired depth. The laser may also be operated in a non-gated pulsed mode where pulses repeat every five milliseconds as long as the laser is actuated. Operating in this mode while sweeping the handpiece 18 over the target tissue enables the operator or user to ablate even larger areas more efficiently and uniformly than is possible using a small spot size. The gating signal can also be modulated on and off while operating in this mode for lower ablation rates and more precise control. For example, if the laser is modulated on and off in 60 millisecond intervals, the range of average power would be reduced by half, from 5.0 to 9.0 watts down to 2.5 to 4.5 watts.

While a preferred embodiment of the invention has been illustrated and described, it is to be understood that various changes may be made therein without departing from the spirit and scope of the invention. For instance, in addition to $CO_2$ laser systems, this invention would also be particularly useful for reducing the size of an Er:YAG laser system used to ablate hard tissue. Consequently, the invention is to be limited only by the scope of the claims that follow.

The embodiments of the invention in which an exclusive property or privilege is claimed are defined as follows:

1. A method for scanning laser energy at a target site, the laser energy being delivered to the target site through a conduit for conducting laser energy, the conduit having a proximal end in light energy communication with a laser energy source and a distal end for delivery of laser energy, the method comprising the step of:

uniformly moving the conduit in a predetermined pattern to thoroughly scan the target site with laser energy in order to uniformly ablate tissue by maintaining the proximal end of the conduit in fixed alignment with the laser energy source and the distal end of the conduit out of alignment with the laser energy source and rotating the conduit about its longitudinal axis to move the distal end of the conduit in the predetermined pattern.

2. The method of claim 1, wherein the step of uniformly moving the conduit further comprises holding the conduit in a predetermined shape with the proximal end in fixed alignment with the laser energy source such that the distal end is rotated in the predetermined pattern.

3. A method for delivering pulses of laser energy at a target site, comprising the steps of:

generating pulses of laser energy of a predetermined power and duration; and scanning the pulses of laser energy through a conduit having a proximal end, a distal end, and a longitudinal axis, by maintaining the distal end of the conduit off center with respect to the longitudinal axis of the conduit at the proximal end and rotating the conduit about its longitudinal axis to move the distal end of the conduit in a predetermined pattern and at a predetermined speed at the target site to uniformly ablate tissue at the target site.

4. A laser delivery system for delivering laser energy to a target site, the system comprising:

means for generating laser energy; and means for scanning the laser energy, at the target site, said scanning means comprising:

a conduit for conducting laser energy, said conduit having an elongated shape with a proximal end, a distal end and a longitudinal axis; and means for moving said conduit in a predetermined pattern to uniformly scan the target site with laser energy, said conduit mounted on said moving means such that said proximal end of said conduit is in light energy communication with said means for generating laser energy, and said distal end of said conduit is mounted on said moving means to be off-center in relation to a rotational axis of said moving means, whereby said moving means rotates said conduit about its longitudinal axis so that said distal end is moved in a circular pattern.

5. The system of claim 4, wherein said distal end of said conduit has a substantially teardropped shaped cross-sectional configuration.

6. The system of claim 4, wherein said generating means is configured to generate pulses of energy of a predetermined power and duration, and said moving means is configured to move said conduit at a predetermined speed such that the laser energy is delivered uniformly to the target site.

7. A laser delivery system for delivering laser energy to a target site, the system comprising:

means for generating laser energy;

means for scanning the laser energy at the target, said scanning means comprising:

means for conducting the laser energy from said laser energy generating means;

a conduit for conducting laser energy from said conducting means to the target site, said conduit having a proximal end, a distal end, and a longitudinal axis; and means for moving said conduit in a predetermined pattern to uniformly scan the target site with laser energy, said moving means comprising a motor having a hollow shaft mounted therein to rotate about its longitudinal axis, and further wherein said conduit is mounted on said hollow shaft such that said proximal end of said conduit is in light energy communication with said conducting means and said distal end of said conduit is misaligned with the longitudinal axis of said hollow shaft such that as said motor rotates said hollow shaft, said distal end of said conduit moves in a predetermined pattern.

8. The system of claim 7, wherein said distal end of said conduit has a substantially tear-dropped shaped cross-sectional configuration.

9. A laser scanning device for delivering laser energy from a laser energy source to a target site, comprising:

a conduit for conducting laser energy to the target site, said conduit having a proximal end in laser energy communication with the laser energy source and a distal end having a predetermined cross-sectional configuration; and means for moving said conduit in a predetermined pattern to uniformly and thoroughly scan the target site with laser energy, said moving means comprising a hollow shaft that rotates about its longitudinal axis, said distal end of said conduit being mounted on said hollow shaft such that said distal end is eccentric with respect to the longitudinal axis of said hollow shaft.

10. The device of claim 9, wherein said cross-sectional configuration of said distal end of said conduit is substantially in the shape of an isosceles triangle having its apex at least adjacent to the longitudinal axis of said hollow shaft.

11. The device of claim 9, wherein said cross-sectional configuration of said distal end of said conduit is substantially in the shape of a teardrop having its apex adjacent to the longitudinal axis of said hollow shaft.

12. The device of claim 9, wherein the laser energy source generates pulses of laser energy having a predetermined power and length of duration, and further wherein said moving means is configured to move said conduit at a predetermined speed so that the laser energy is delivered uniformly to the target site.

13. The device of claim 9, further comprising a hand-holdable housing in which said moving means is mounted.

14. The device of claim 13, wherein said hand-holdable housing further includes means for aligning the device with the target site.

15. A laser delivery system for delivering laser energy to a target site, the system comprising:

means for generating laser energy, said laser energy generating means configured to generate pulses of laser energy of a predetermined power and duration;

means for scanning the laser energy at the target site, said scanning means comprising;

means for conducting the laser energy from said laser energy generating means;

a conduit for conducting laser energy, said conduit having a proximal end and a distal end, and a longitudinal axis;

means for moving said conduit in a predetermined pattern to uniformly scan the target site with laser energy, said moving means configured to move said conduit at a predetermined speed such that the laser energy is delivered uniformly to the target site, said conduit is mounted on said moving means with the proximal end in light energy communication with said conducting means and rotates about its longitudinal axis, and said distal end is mounted to be off-center in relation to a rotational axis of said moving means whereby said moving means rotates said distal end in a circular pattern.

16. A laser delivery system for delivering laser energy to a target site, the system comprising:

means for generating laser energy, said generating means being configured to generate pulses of laser energy of a predetermined power and duration; and means for scanning the laser energy at the target site, said scanning means comprising:

means for conducting the laser energy from said laser energy generating means;

a conduit for conducting laser energy from said conducting means to the target site, said conduit having a proximal end, a distal end, and a longitudinal axis; and means for moving said conduit in a predetermined pattern to uniformly scan the target site with laser energy, said moving means configured to move said conduit at a predetermined speed such that the laser energy is delivered uniformly to the target site, said moving means further comprising a motor having a hollow shaft mounted therein to rotate about its longitudinal axis, and further wherein said conduit is mounted on said hollow shaft such that said proximal end of said conduit is in light energy communication with said conducting means and said distal end of said conduit is misaligned with a longitudinal axis of said hollow shaft such that as said moving means rotates said hollow shaft, said distal end of said conduit moves in a circular pattern.

* * * * *